United States Patent [19]

Giroir

[11] 4,409,184
[45] Oct. 11, 1983

[54] PARAFFIN WRINKLE AND BUBBLE REMOVER APPARATUS

[76] Inventor: William Giroir, 3001 B Independence St., Metairie, La. 70002

[21] Appl. No.: 348,746

[22] Filed: Feb. 16, 1982

Related U.S. Application Data

[62] Division of Ser. No. 181,967, Aug. 28, 1980, Pat. No. 4,357,302.

[51] Int. Cl.³ .............................................. B01L 9/00
[52] U.S. Cl. ...................................... 422/99; 81/3 R; 81/43; 128/354; 422/104
[58] Field of Search ................. D28/55; 81/43, 3 R; D24/99, 8, 29; 422/99, 104; 29/281.5; 223/61; 38/69, 70; 7/158, 162, 900; 128/354, 321, 303 R, 356, 61, 62 R, 51, 52, 3, 20; 294/99 R

[56] References Cited

U.S. PATENT DOCUMENTS

| 244 | 6/1837 | Flint | 81/43 |
|---|---|---|---|
| D. 55,482 | 6/1920 | Rozenske | D28/55 |
| D. 159,612 | 8/1950 | Henkel | D28/55 |
| D. 192,520 | 4/1962 | Harano | D28/55 |
| 783,244 | 2/1905 | Burns | 81/43 |
| 928,424 | 7/1909 | Betts | 223/61 |
| 1,655,962 | 1/1928 | Lespinasse | 128/321 X |
| 2,234,715 | 3/1941 | Whitney | 81/43 X |
| 2,452,332 | 10/1948 | Siptrott | 81/3 R X |
| 2,456,806 | 12/1948 | Wolffe | 128/127 X |
| 3,306,139 | 2/1967 | Prackett | 81/43 |
| 4,300,564 | 11/1981 | Furihata | 128/321 |

*Primary Examiner*—Kenneth M. Schor
*Attorney, Agent, or Firm*—Bode & Smith

[57] ABSTRACT

A hand held apparatus having a generally J-shape for removing wrinkles and bubbles in a thin paraffin ribbon having a pair of normally flexible handles and a pair of elongated strut members with the handles, disposed at an angle in relation to the handles and movable with respect to one another, responsive to a flexing of handles. The apparatus also includes a pair of spreader portions disposed at the opposite end of the strut members in relation to the handles, and a pair of spreader pad portions attached to the top end portions of the strut members so that flexing of the handles brings the spreader portions in close relation to one another, and unflexing of the handles brings the spreader portions apart, thus spreading the thin paraffin layer as the spreader portions are separated.

3 Claims, 9 Drawing Figures

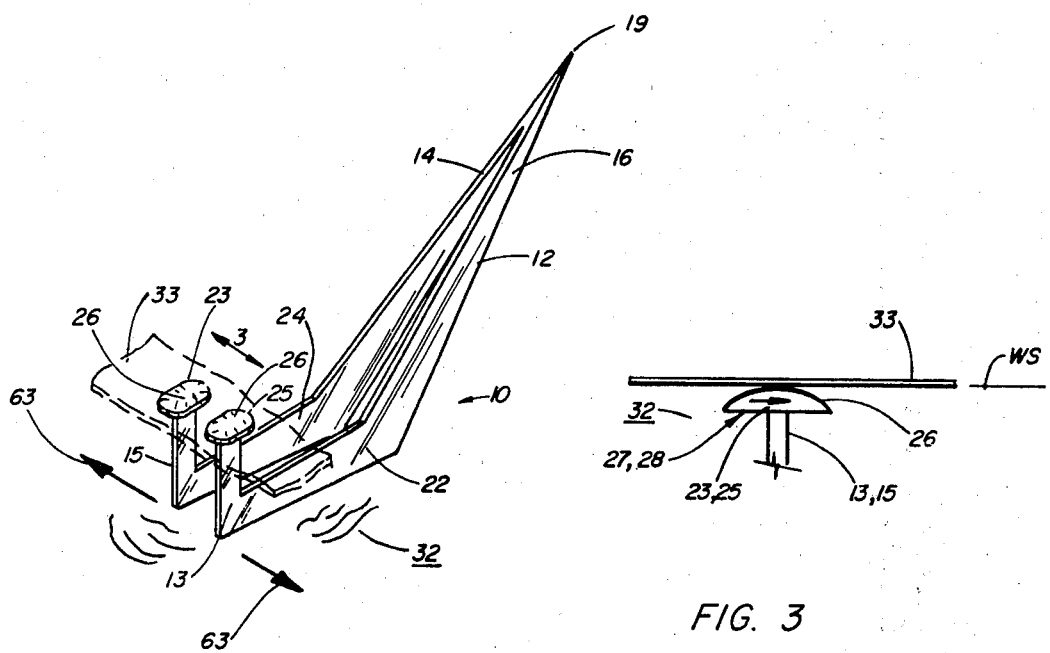
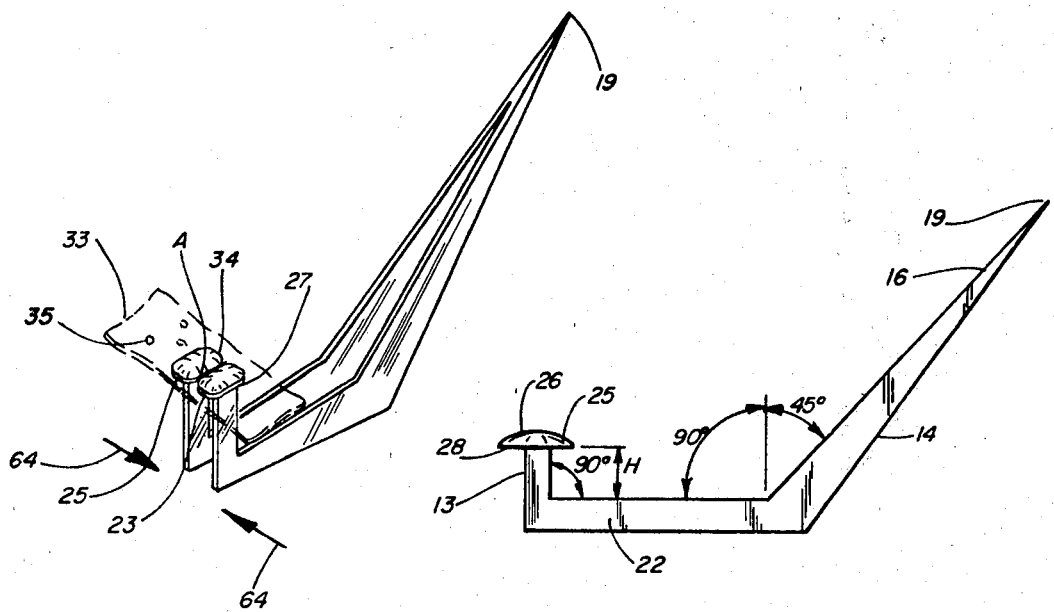
FIG. 1
FIG. 3
FIG. 2
FIG. 4

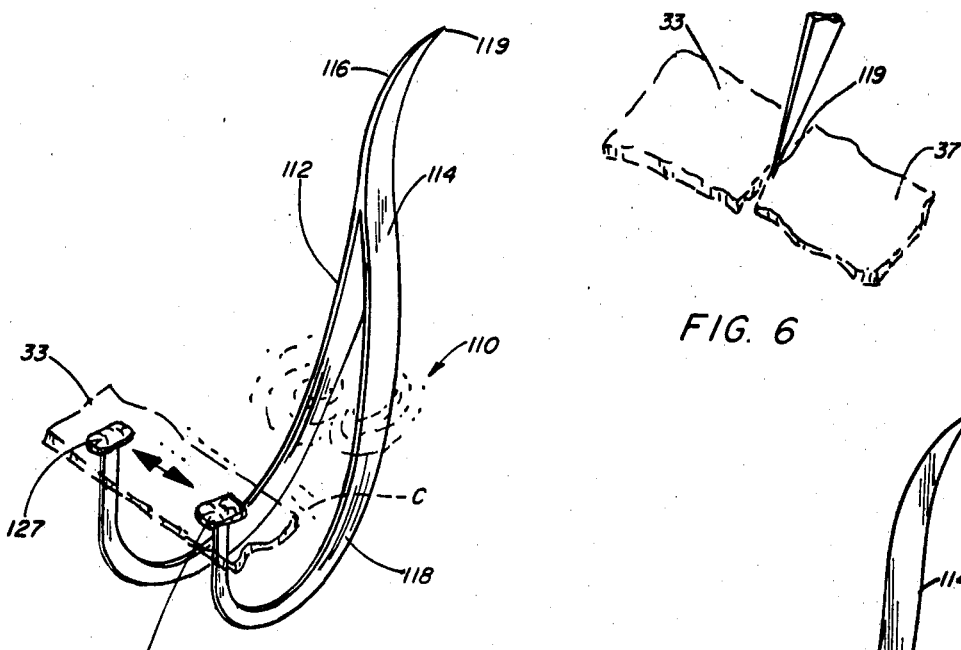
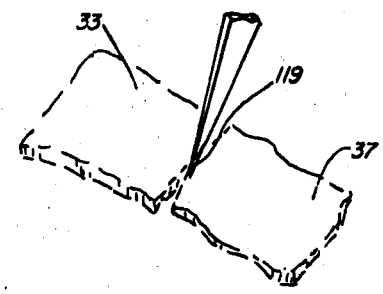
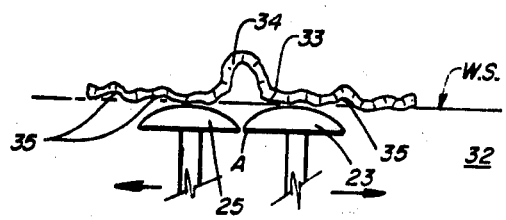
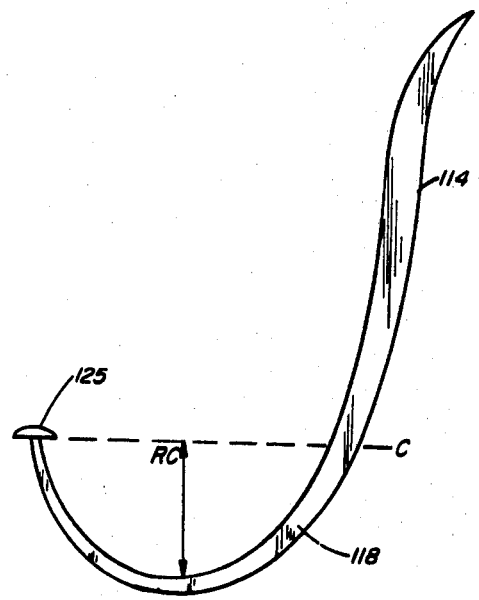
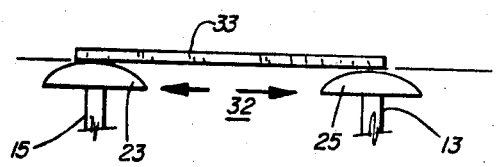

PARAFFIN WRINKLE AND BUBBLE REMOVER APPARATUS

This is a division of application Ser. No. 181,967, filed Aug. 28, 1980 and titled "PARAFFIN WRINKLE AND BUBBLE REMOVER APPARATUS" by the same inventor, which is now U.S. Pat. No. 4,357,302.

BACKGROUND OF THE INVENTION

1. Field of the Invention

The present invention relates to laboratory instruments. More particularly, the present invention relates to an apparatus for removing wrinkles and bubbles in a paraffin ribbon set upon a water bath.

2. General Background

Whenever a section of tissue, organs or any part of the human body is removed through the process of surgery, a specimen or part of the specimen is sent to the histology laboratory for processing into microscopic slide examinations. Through a series of dehydrating alcohols and clearing chemicals, for example, dioxane, zylene, or benzene, the tissue specimen is impregnated with a non-water soluble wax called paraffin (paraplast). The specimen tissue is then completely encased in a block of the paraffin paraplast. It is mounted on a microtome and sliced at four to ten microns in thickness.

Due to the up and downward motion of the microtome block holder shaft, a paraffin ribbon is formed on the microtome knife. Each paraffin section adheres to the edge of the one preceding it. This extended ribbon, made up of the various paraffin sections connected end to end, is spread on a water bath with the water temperature at approximately 34-38 degrees Centigrade. The warm water assists in spreading out the ribbon and removing wrinkles from the paraffin wax. However, many smaller wrinkles and air bubbles are trapped in the sections while it is being laid on the water bath surface.

Presently, several items are utilized in the histology laboratory for removing these tiny wrinkles and bubbles from the paraffin ribbons, including, an artist's camel hair brush, a metal probe which resembles a mini "ice pick", the technician's fingers and cotton swabs.

Each of these methods have encountered various problems, mostly having to do with the inefficiency and cumbersomeness with which these particular apparatus have to be utilized over the delicately and thinly cut paraffin ribbon. However, in each of these methods, if the device utilized would have the slightest catch onto the paraffin ribbon, it would completely destroy the ribbon, and the paraffin mount would have to be redone.

Other methods would include the technician removing the wrinkles and bubbles by stretching out the paraffin ribbon until most of the wrinkles are out. Again, this works to a certain extent. However, by stretching the paraffin ribbon, the technician would start to separate the specimen to be examined. The specimen has been infiltrated with paraffin, so as the technician would pull on the ribbon, the specimen would crack and tear. This would create gaps and cracks which the pathologist must proportion back together under the microscope. Such an undertaking would be tedious and time consuming.

The present apparatus would solve the technician's problem in removing wrinkles and bubbles in paraffin ribbons with the use of a forceps-like apparatus. Some patents demonstrate forcep structures as follows:

U.S. Pat. No. 2,587,486, entitled "Cervical Speculum" issued to J. Kogan would teach the use of an apparatus having a pair of handles, a pivot connecting said handles and a blade portion connected to each of the handles and extending on the opposite side of the pivot. The use of the instrument would be for dilating the mouth of the cervical canal by extending out the handle proportions of the apparatus.

U.S. Pat. No. 1,386,436, entitled "Dental Pliers" issued to W. C. Smith would teach the use of pliers particularly adapted for use by dentists in handling small particles of material for a positive grip is desirable and accuracy in application necessary. The improved pliers are formed from a single piece of metal intermediately bent to provide opposing jaws which are reduced in thickness and terminated the free ends of the jaws in laterally and obliquely projected beaks.

U.S. Pat. No. 3,980,861, entitled "Electrically Heated Miniature Thermal Implement" issued to A. Fukunaga, would teach the use of a miniature thermal wire strip having a pair of heater elements in the form of hollow tubes, each with a heater coil disposed therein in a fixture with a pair of spring loaded handles for contacting and subsequently melting through thermal insulation about a wire from which insulation is to be stripped.

U.S. Pat. No. 1,510,254 entitled "Pliers" issued to J. O. Boyle would teach the use of an instrument consisting of a pair of resilient, swingable arms, each having a pair of spacer spreader arms provided with teeth, the resilient and mounted arms being adapted to be moved into engagement with each other to permit insertion of the spreader arms into the incision so that the teeth may engage walls of the incision or may engage the skin for spreading the walls apart.

U.S. Pat. No. 2,634,728 entitled "Hair Tweezers" issued to G. T. Dale would teach the use of tweezers within the gripping portion of the tweezers are held in positive engagement with each other under spring pressure and the gripping action does not depend on the user holding the tweezers closed.

3. General Discussion of the Present Invention

The apparatus of the present invention provides a hand held apparatus for removing wrinkles in a think paraffin ribbon. The apparatus would have a pair of flexible normally angularly spaced handles connected at one end portion. Set upon other end portions of each handle would be an elongated strut portion forming an integral section with the handles and disposed at an angle in relation to the longitudinal axis of the handles. The strut members would form an integral projection with spreader portions disposed at the other end of the strut members and at an angle to the strut members. The spreader portions would generally comprise a spreader arm forming a support for a spreader pad, the latter being fixedly connected at the top portion of the spreader arm. The spreader pads would be substantantially convex on the top surface and connected to the spreader arm midway along the lowers surface. The top surface of the spreader pads would also be coated with a paraffin non-adhesive material. In the operation, the handles would maintain the spreader arms apart from one another. Upon contraction of the handles, the spreader arms and spreader pads would move together and align themselves to form a spreader surface upon which the underside of the paraffin ribbon would rest against. The arms would then be allowed to reflex back to their normal position, thus the spreader pads moving outward away from one another spreading the paraffin ribbon smooth. The top free end of the handle portions would be tapered off into a needle point, so that the paraffin ribbon, which are connected end to end, could be separated from one another with the pointed end.

Thus, it is an object of the present invention to provide a hand held device useful in the preparation of paraffin ribbon type microscopic slides.

It is another object of the present invention to provide a method for removing bubbles and the like from microscopic slide paraffin ribbons during the slide preparation stage.

Another object of the present invention is to provide a device for removing bubbles and wrinkles from paraffin ribbons while supported on a water bath and prior to microscopic slide mounting.

It is another object of the present invention to provide a microscopic slide paraffin ribbon manipulating device which is easy to use and simple in operation.

Another object of the present invention is to provide a device useful in the preparation of paraffin ribbons for mounting on microscopic slides which both flattens and removes wrinkles and bubbles from the paraffin ribbon on a water bath as well as provides means for cutting excess portions of the paraffin ribbon from the useful portion.

It is another object of the present invention to provide a spreader device for use in preparation of microscopic slide paraffin ribbons which does not adhere to the paraffin ribbon during the manipulation thereof.

BRIEF DESCRIPTION OF THE DRAWINGS

For a further understanding of the nature and object of the present invention, reference should be made to the following detailed description, taken in conjunction with the accompanying drawings, in which like parts are given like reference numerals and wherein:

FIG. 1 is a perspective view of the preferred embodiment of the apparatus of the present invention;

FIG. 2 is another perspective view of the preferred embodiment of the apparatus of the present invention with the forceps collapsed;

FIG. 3 is a detailed partial side view of the spreader portion of the preferred embodiment of the apparatus of the present invention;

FIG. 4 is a side view of the preferred embodiment of the apparatus of the present invention;

FIG. 5 is perspective view of the second preferred embodiment of the apparatus of the present invention;

FIG. 6 is a partial perspective view of the cutting tip portion of the preferred embodiment of the apparatus of the present invention; and FIG. 7 is a side view of the second preferred embodiment of the apparatus of the present invention.

FIG. 8 is a side view of the spreader portions of the apparatus proximate one another set against the paraffin ribbon;

FIG. 9 is a side view of the spreader portion of the apparatus extended against the paraffin layer.

DETAILED DESCRIPTION OF THE PREFERRED EMBODIMENT

FIG. 1 best illustrates the preferred embodiment of the apparatus of the present invention designated generally by the numeral 10. In FIG. 1 there can be seen handles 12 and 14 which are preferably integrally connected at one end portion 16 and tapering off into needlepoint end 19. As will be described more fully hereinafter, needlepoint 19 can be utilized in separating the sections of paraffin ribbons after they have been laid upon water bath 32.

Water bath 32 would normally be provided in the preparation of microscopic slides when a paraffin ribbon were used. It is known in the art to prepare thin paraffin ribbons by cutting them in very thin (for example, a few microns in thickness) which sections are then mounted on the surface of a water bath. In FIGS. 1, 2 and 3, a water bath 32 has been schematically illustrated having a water surface WS.

Strut members 22, 24 are preferably integrally attached to handles 12, 14 respectively. Note from an inspection of FIG. 4 that handle 14 is angularly disposed to strut member 22 with an angle of 135 degrees being preferable.

At the other end portion of each strut member 22, 24 there is preferably integrally formed therewith at, for example, 90 degree angles thereto, a pair of vertically disposed spreader arms 13, 15. Each spreader arm 13, 15 as best seen in FIGS. 1 and 2 connects integrally to its respective strut member 22, 14.

Vertical spreader arms 13, 15 would support spreader pad portions 23 and 25 which could be of circular, rectangular, oval or the like in shape, the preferred embodiment indicating that the rectangular configuration as illustrated in FIG. 1 would be the preferred shape. Spreader pads 23 and 25 would have a convex upper surface 26 (FIG. 3) which in use would abut against the bottom surface of paraffin wax ribbon 33 and would be connected to spreader arms 13, 15 on the flat lower surface 27, 28 of spreader pads 23 and 25. Arrows 63 indicate the ability of handles 12 and 14 to move into and away from one another in a flexing movement. FIG. 1 shows a normal "spaced" position which handles 12, 14 would assume absent force applied by hand. In FIG. 2, handles 12, 14 are collapsed and moved inwardly as illustrated by arrows 64. Handles 12, 14 would be of a spring wheel such as stainless steel or the like, and this biasing to the spaced normal position could be overcome by applying hand force as with conventional tweezers.

FIG. 2 would illustrate apparatus 10 with handles 12, 14 in the collapsed position. Note that in the collapsed position, vertical spreader arms 13, 15 are brought adjacent one another to a point that the spreader pad 23, 25 portions are making contact with and abutting one another at point A and would in effect create a continuous spreader pad surface. In FIGS. 1-3 is paraffin ribbon 33 as it would be set upon water bath 32. In FIG. 2, paraffin ribbon 32 has a wrinkle 34 and bubbles 35 which are typically encountered in the preparation of such paraffin ribbon slide mounts at the water bath stage. In FIG. 1, handles 12, 14 would then be allowed to unflex with the user relaxing hand held pressure allowing handles 12, 14 to diverge similarly and therewith spreader pads 23, 25 diverge having the effect of smoothing the undersurface of paraffin ribbon 33 in the process to remove wrinkle 34.

FIG. 2 would illustrate a side view of apparatus 10 showing the distal end portion 16 of apparatus 10 which would taper off into needlepoint 19 for perforating, serrating and separating the excess portions of paraffin ribbon 33, prior to mounting ribbon 33 on a slide as would be more clearly illustrated in FIG. 4.

FIGS. 5-7 indicate a second preferred embodiment of the apparatus of the present invention designated generally as 110. As can be seen from the drawings, the apparatus is generally J-shaped. This particular embodiment of the apparatus 110 would also include handles 112 and 114 connected at the proximate end portion 116, with the ability for flexing away from one another. It should be noted also that proximate end 116 also provides needlepoint 119 for separation of the paraffin ribbon on the water bath as with the embodiment of FIGS. 1–4.

In this embodiment (FIGS. 5–7) note that handles 112 and 114 are curved and would be integrally attached to arcuate recurved section 118, 119 of handles. Recurved sections 118, 119 are generally shown below dotted line C (FIG. 5). In this particular embodiment, it should be noted that the hand held section of handles 112 and 114 would have the ability to be held above water and operated thusly without the operator's hand having to go beneath the surface of the water, similar to the preferred embodiment of FIGS. 1–4.

FIG. 6 would illustrate needlepoint 119 of apparatus 110 as it would be perforating and serrating paraffin ribbon 33, allowing paraffin ribbon 33 to be separated from the next paraffin ribbon section 37 which would be attached thereto after having been sliced from the paraffin block. Needlepoint 119 contained on proximate end portion 116 of apparatus 110 would essentially enable an operator to utilize the same apparatus in performing both the functions of separating the paraffin ribbon from one another and removing the wrinkles and bubbles from the layer of paraffin 33 which would be set upon water bath 32.

FIG. 7 illustrates the location of spreader pads 125, 127, as seen in side view and its geometric relationship to the handle portions 112, 114. It should be noted that the location of spreader pad 125 is somewhat below the handle portion of the apparatus as indicated by the dotted line extending on the axis perpendicular to the handle portion of said apparatus. This particular structure of the apparatus would be the enabling factor of maintaining the operator's hand above water while manipulating the apparatus for spreading the paraffin ribbon as shown in FIG. 3. Arcuate recurved section 118 which is integrally attached to handle 114 would essentially be that section of the apparatus extending below line C through the arcuate to spreader pad 125. A radius of curvature RC equal to one inch would be exemplary.

It should be made clear that the flexing of the apparatus would be in its normal position with the spreaders apart from one another so that the operator would have to hand hold handles 112, 114 and bring them together in order to get spreader pads 125, 127 in a position for making contact with the paraffin ribbon and thus releasing the tension on handles 112 and 114 to enable them to move apart again and spread paraffin ribbon 33 out, thus removing any bubbles or wrinkles.

FIGS. 8 and 9 illustrate in sequence the removal of either a wrinkle 34 or a bubble 35 from paraffin ribbon 33 as it sits upon water bath 32. The water surface WS of water bath 32 is shown as was illustrated in FIG. 3.

FIG. 8 shows a wrinkle 34 and three bubbles 35 in a schematic sectional fashion. Note that spreader pads 23, 25 have been moved in proximity together at point A. This position is achieved as aforementioned by applying hand pressure to handles 12, 14 so that they are brought together or collapsed as is also shown in FIG. 2.

In FIG. 9, the user has released hand pressure on handles 12, 14 allowing divergence of handles 12, 14 as well as allowing for divergence of pads 23, 25. Since each pad 23, 25 is placed into frictional engagement with the bottom surface of paraffin ribbon 33, as the divergence of pads 23, 25 occurs, it urges the end portions of ribbon 33 apart thus removing wrinkle 34 and providing a straight flat ribbon 33 as seen in FIG. 9.

In a like fashion, the spreader pads 23, 25 can engage any bubbles 35 and urge them outwardly until the periphery of ribbon 33 is reached, disposing of bubbles 35 therefrom. In this manner, wrinkles 34 and bubbles 35 can be removed by repeated collapsing and spreading of handles 12, 14 by the user with pads being removed from ribbon 33 during the collapsing of handles 12, 14 and with pads 23, 25 being gently engaged to the bottom surface of ribbon 33 during the diverging thereof as shown in FIGS. 8 and 9.

Normally, ribbon 33 would be supported upon the water surface WS of water bath 32 by surface tension, for example, due to its very thin and very light construction.

Because many varying and different embodiments may be made within the scope of the inventive concept herein taught, and because any modifications may be made in the embodiments herein detailed in accordance with the descriptive requirement of the law, it is to be understood that the details herein are to be interpreted as illustrative and not in a limiting sense.

What is claimed as invention is:

1. A hand held apparatus for removing wrinkles and bubbles in a thin paraffin ribbon, said hand held apparatus having a substantially J-shape and comprising:
   a. a pair of normally flexible handles integrally connected together at one end portion of the hand held apparatus and each of said handles integrally connected to an arcuate portion, the arcuate portions providing support to spreader pad portions movable with respect to one another responsive to a flexing of said handles, with said arcuate portions extending downwardly from said handles and then arcing upwardly to support said spreader pad portions;
   b. each spreader pad portion being connected to and disposed at the end of each of the arcuate support portions which is not connected to the handles, in such a manner that its top surface is perpendicular to the longitudinal axis of said handle and substantially spaced apart from said handle, wherein each spreader pad portion has a top surface capable of frictionally engaging and supporting, for spreading, a portion of said paraffin ribbon, and where the top surfaces of the spreader pad portions are alligned such that they can spread said ribbon upon flexing of said handles.

2. The apparatus of claim 1, wherein each of said spreader pad portions further comprise a substantially convex top surface and is connected to said end of arcuate sections midway along the lower surface.

3. The apparatus of claim 1, wherein said top surface of said spreader pad portion is coated with a paraffin non-adhesive material.

* * * * *